(12) United States Patent
Ghasemzadeh et al.

(10) Patent No.: US 9,754,081 B2
(45) Date of Patent: Sep. 5, 2017

(54) CONTEXT-AWARE PREDICTION IN MEDICAL SYSTEMS

(71) Applicant: THE REGENTS OF THE UNIVERSITY OF CALIFORNIA, Oakland, CA (US)

(72) Inventors: Hassan Ghasemzadeh, Valley Village, CA (US); Myung-Kyung Suh, Los Angeles, CA (US); Mars Lan, Los Angeles, CA (US); Majid Sarrafzadeh, Anaheim Hill, CA (US); Nabil Alshurafa, Camarillo, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 503 days.

(21) Appl. No.: 14/276,660

(22) Filed: May 13, 2014

(65) Prior Publication Data

US 2014/0344208 A1 Nov. 20, 2014

Related U.S. Application Data

(60) Provisional application No. 61/823,230, filed on May 14, 2013.

(51) Int. Cl.
*G06N 7/00* (2006.01)
*G06F 19/00* (2011.01)
(52) U.S. Cl.
CPC ................ *G06F 19/3437* (2013.01)
(58) Field of Classification Search
CPC ....... G06F 19/3437; G06N 7/02; G06N 7/005

USPC .......................................................... 706/52
See application file for complete search history.

(56) References Cited

U.S. PATENT DOCUMENTS 7,505,867 B2 3/2009 Bharara et al.
7,899,225 B2 3/2011 Collins et al.
(Continued)

OTHER PUBLICATIONS

Lambin et al. (Lambin12), Predicting outcomes in radiation oncology—multifactorial decision support systems [online], published online Nov. 20, 2012 [retrieved on May 18, 2016]. Retrieved from the Internet:<URL:http://www.nature.com/nrclinonc/journal/v10/n1/pdf/nrclinonc.2012.196.pdf>.*

(Continued)

*Primary Examiner* — Dave Misir
(74) *Attorney, Agent, or Firm* — Foley & Lardner LLP; Cliff Z. Liu

(57) ABSTRACT

A method includes receiving contextual data related to at least one of environmental, physiological, behavioral, and historical context, and receiving outcome data related to at least one outcome. The method further includes creating a feature set from the contextual data, selecting a subset of features from the feature set, assigning a score to each feature in the subset of features according to the probability that the feature is a predictor of the at least one outcome, and generating a characteristic curve for the at least one outcome from the subset of features, the characteristic curve being based on the scoring. The method further includes calculating the area under the characteristic curve, and using, the area under the characteristic curve, identifying whether the subset of features is a suitable predictor for the at least one outcome.

17 Claims, 11 Drawing Sheets

(56) References Cited

U.S. PATENT DOCUMENTS

| | | |
|---|---|---|
| 2007/0100666 A1 | 5/2007 | Stivoric et al. |
| 2009/0105573 A1 | 4/2009 | Malecha |
| 2009/0192394 A1 | 7/2009 | Guttag et al. |
| 2010/0088264 A1* | 4/2010 | Teverovskiy ......... G06F 19/345 706/46 |
| 2011/0046805 A1 | 2/2011 | Bedros et al. |
| 2011/0225114 A1 | 9/2011 | Gotthardt |
| 2012/0071731 A1 | 3/2012 | Gottesman |
| 2012/0114211 A1 | 5/2012 | Kraus et al. |
| 2013/0196868 A1* | 8/2013 | Lebowitz ........... G01N 33/6893 506/9 |

OTHER PUBLICATIONS

Ghasemzadeh H. et al., "Energy-Efficient Signal Processing in Wearable Embedded Systems: An Optimal Feature Selection Approach", ISLPED'12, Jul. 30-Aug. 1, 2012, Redondo Beach, CA, USA.*

International Preliminary Report on Patentability (IPRP) and Written Opinion for International Application No. PCT/US2014/037887 mailed Nov. 26, 2015.

International Search Report and Written Opinion (ISA/KR) for International Application No. PCT/US2014/037887 mailed Oct. 10, 2014.

Dragulescu et al., "Medical Predictions System," Journal of Acta Polytechnica Hungarica, vol. 4(3), (2007), pp. 89-101.

\* cited by examiner

CONTEXT-AWARE PREDICTION IN MEDICAL SYSTEMS

CROSS-REFERENCE TO RELATED PATENT APPLICATIONS

This application claims the benefit of U.S. Provisional Patent Application 61/823,230 filed May 14, 2013 to Ghasemzadeh et al., titled "Context-Aware Prediction in Medical Systems," the contents of which are incorporated herein by reference in their entirety.

BACKGROUND

Prediction, such as prediction of efficacy of a course of action or prediction of a future outcome, is often inaccurate, and therefore improved techniques for prediction would be beneficial.

SUMMARY

In one aspect, a method includes receiving contextual data related to at least one of environmental, physiological, behavioral, and historical context, receiving outcome data related to at least one outcome, creating a feature set from the contextual data, selecting a subset of features from the feature set, and assigning a score to each feature in the subset of features according to the probability that the feature is a predictor of the at least one outcome. The method further includes generating a characteristic curve for the at least one outcome from the subset of features, the characteristic curve based on the scoring, calculating an area under the characteristic curve, and identifying, using the area under the characteristic curve, whether the subset of features is a suitable predictor for the at least one outcome.

In one aspect, a system includes a memory including processor-executable instructions and a processor configured to execute instructions from the memory. The instructions include instructions for the processor to receive contextual data and outcome data, create a feature set from the contextual data, and select a plurality of feature subsets from the feature set. For each of the plurality of feature subsets, the instructions include instructions to apply the feature subset and the outcome data to a classifier, and determine a score for the feature subset, select a preferred feature subset based on the score for each of the plurality of feature subsets, and generate a prediction model using the preferred feature subset.

In one aspect, a processor-readable physical medium includes processor-executable instructions. The instructions include instructions for receiving outcome information and contextual information related to the outcome information, pre-processing the outcome information and contextual information, and creating a feature set from the pre-processed contextual information. The instructions further include instructions for assigning scores to at least some of the features in the feature set, wherein a score is assigned to a feature according to the ability of the feature to predict an outcome described by the outcome information, determining a set of characteristic curves using the scores, wherein each characteristic curve represents an ability to predict the outcome, calculating a score for each of the characteristic curves in the set of characteristic curves, and based on the score for each of the characteristic curves, identifying a predictor including features from the feature set.

DETAILED DESCRIPTION

The present disclosure describes context-aware prediction of medical conditions or events. Prediction based on physiological data alone is not always effective without knowing the context of the data. Studies have shown evidence that there is a correlation between some contextual data and some medical conditions, such as in the following examples: traffic-related air pollution around a child's residence can cause repeated hospitalization for children with asthma; weight loss and exercise can reduce the risk of diabetes; certain genes can be responsible for production of protein substances (e.g. C-Reactive Protein) that may result in an increased risk of heart attacks in coronary artery disease patients. As another example, a high pulse rate may be predictive of a health condition, but if in context the high pulse rate was due to recent physical activity, then the prediction would be incorrect.

In addition to providing predictions for medical conditions, context-aware prediction may provide community-based conclusions useful, for example, in policy-making related to health management or preventive medicine. Examples of community-based conclusions include a finding that sports participants are more motivated to engage in sports as a means for social enjoyment rather than to achieve positive health benefits; and that seasonal variation in blood pressure is greater in older subjects and is related to maximum and minimum daily air temperatures.

Context-aware prediction may further provide benefit by improving prediction accuracy and response time through narrowing of a solution space. For example, certain biomarkers can help to classify a hepatitis virus in a patient as being one of the group B, B+D, or C, and logical inference may then be used to decide which of hepatitis virus B, B+D or C is present. Prediction with respect to treatment efficacy may include evolution of biological parameters using artificial neural networks.

Figure 1:
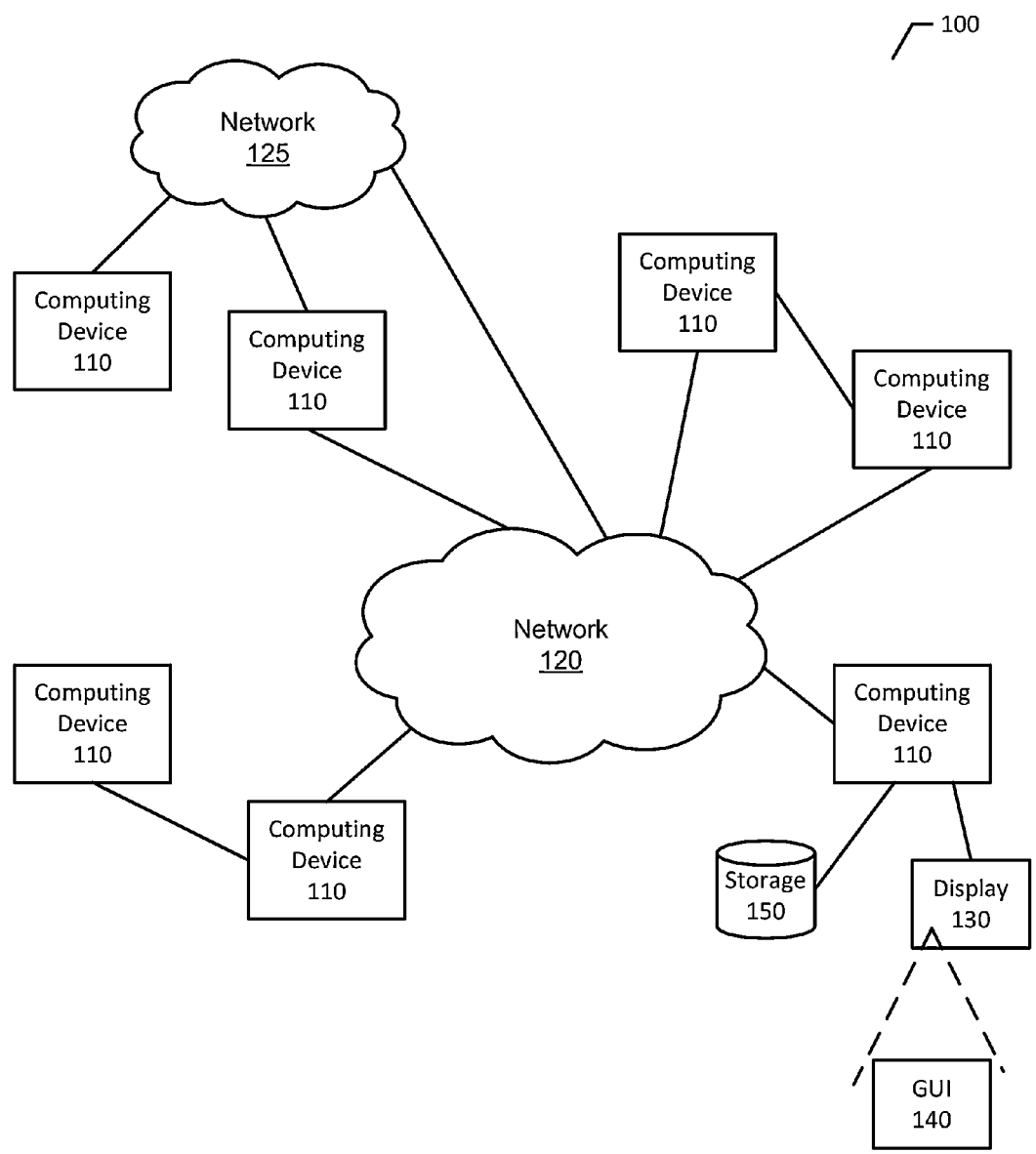
FIG. 1 illustrates an example of a system for context-aware prediction.

FIG. 1 illustrates an embodiment of a context-aware prediction system 100 according to this disclosure. A computing device 110 may be in communication with other computing devices 110 over a network such as network 120 or 125. For example, one computing device 110 at one location may provide information to another computing device 110 at another location, such as providing contextual or outcome information. Computing devices 110 may communicate directly with each other, and one computing device 110 may relay information through another computing device 110.

Computing device 110 may be a device that executes instructions, where the instructions may be in software, hardware, or a combination of software and hardware. Examples of computing devices 110 include, but are not limited to, computers, servers, netbooks, smartphones, personal digital assistants, and so forth. A computing device 110 may include a display 130, with information provided at display 130 via a graphical user interface 140. Instructions may be stored in a storage 150, such as a memory device or unit.

Figure 2:
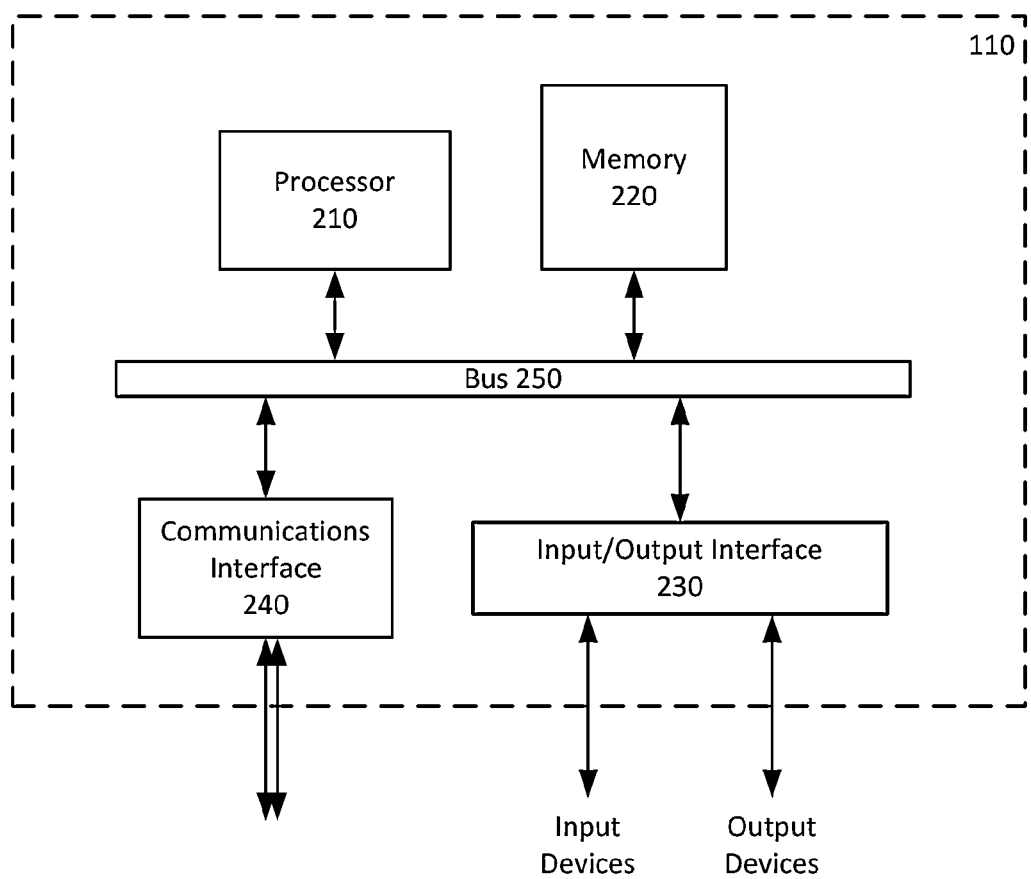
FIG. 2 illustrates an example of a computing device.

FIG. 2 illustrates an example of a computing device 110 that includes a processor 210, a memory 220, an input/output interface 230, and a communication interface 240. A bus 250 provides a communication path between two or more of the components of computing device 110. The components shown are provided by way of illustration and are not limiting. Computing device 110 may have additional or fewer components, or multiple of the same component.

Processor 210 represents one or more of a processor, microprocessor, microcontroller, ASIC, and/or FPGA, along with associated logic.

Memory 220 represents one or both of volatile and non-volatile memory for storing information. Examples of memory include semiconductor memory devices such as EPROM, EEPROM and flash memory devices, magnetic disks such as internal hard disks or removable disks, magneto-optical disks, CD-ROM and DVD-ROM disks, and the like.

The context-aware prediction system of this disclosure may be implemented as computer-readable instructions in memory 220 of computing device 110, executed by processor 210.

Input/output interface 230 represents electrical components and optional code that together provides an interface from the internal components of computing device 110 to external components. Examples include a driver integrated circuit with associated programming.

Communications interface 240 represents electrical components and optional code that together provides an interface from the internal components of computing device 110 to external networks, such as network 120 or network 125.

Bus 250 represents one or more interfaces between components within computing device 110. For example, bus 250 may include a dedicated connection between processor 210 and memory 220 as well as a shared connection between processor 210 and multiple other components of computing device 110.

The present disclosure describes a context-aware prediction system that in one embodiment estimates a likelihood of occurrence of a medical condition, a future adverse event, or medical complications in an individual or group based on data gathered about multiple patients.

Figure 3:
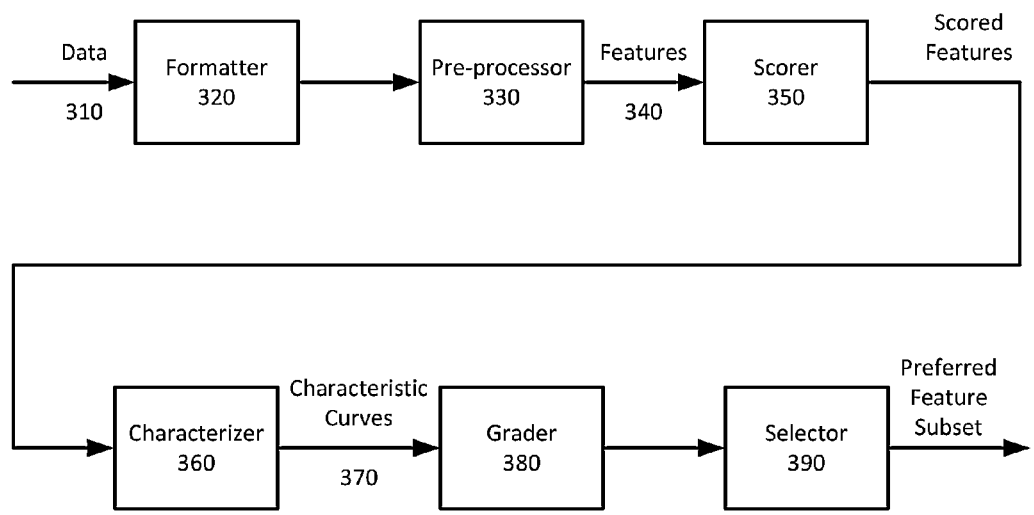
FIG. 3 illustrates an example of a technique for selecting a feature subset.

FIG. 3 illustrates an example of a technique for determining a set of features predictive of an outcome. Data 310 is collected, or retrieved from a storage device. Data 310 includes contextual information and outcome information related to the contextual information. For example, data 310 may include present and historic medical and environmental data for a group of individuals, and one or more pieces of the present medical data may be designated as outcome(s). Data 310 is formatted at block 320, such as by filtering, normalization, and so forth. The formatted data is pre-processed at block 330 to identify a set of features 340 to be used for subsequent processing. Pre-processing includes redundancy elimination and relevance determination, for example. At scorer 350, each feature 340 is scored according to its ability to predict a defined outcome. A score may be, for example, a probability that the feature is able to predict the outcome. At block 360, characteristic curves (CC) 370 are generated based on the feature scores. A CC is generated by setting a feature score threshold to various values, and at each threshold value, for features with scores above the threshold value, determining a true positive rate and a false positive rate of predicting the outcome for data samples related to those features. A plot of true positive rate versus false positive rate for different thresholds is a CC. The CC is graded at block 380, such as by determining the area under the curve (AUC) of the CC.

Grades determined at block 380 may be used in many ways at selector block 390. For the example of AUCs, CCs may be generated for various combinations of scorers 350 and subsets of features 340, and the corresponding AUCs compared to select a combination of a particular scorer 350 and subset of features 340 to use in a prediction model for one or more outcomes. Continuing with this example, a combination may be selected based on its average ability (or other measure) to predict each of multiple outcomes individually, even though its ability to predict one of the multiple outcomes may be less than desirable by itself. As another example, a scorer 350 may be selected by comparing AUCs of two or more scorers 350 for one or more outcomes; or subsets of features 340 may be selected by comparing AUCs of two or more subsets for one or more outcomes.

Weighting may be used to emphasize or de-emphasize particular features or outcomes. For example, a cost of collecting or processing a feature may be considered in assigning a weight. Additional or alternative techniques for selecting features based on cost may be used.

The gathering and processing of data imposes costs on a feature selection technique. There may be time, availability, and transportation costs associated with a person going to a laboratory to have samples taken, or costs associated with privacy issues, in that a person may not want to answer certain questions or provide certain biological samples. There may be computation costs, in that processing power and memory size should accommodate the amount of data gathered. There may be energy costs for sensors and processing in a remote health monitoring (RHM) system, which is especially important for a battery-operated system. These are just a few examples of costs, and there are many other costs that impact a feature selection technique.

Cost-sensitive feature selection aims at minimizing overall cost associated with selection of a subset feature. An approach, discussed below, takes into consideration the cost of individual features. A graph model is introduced to represent correlation and cost of the features. A problem is formulated using integer programming, and a greedy approximation is presented to select the features in a cost-efficient manner. The cost-sensitive approach to feature selection builds a minimized cost feature set while substantially retaining classification accuracy.

For a given scorer 350 and a given subset of features 340, the corresponding CC may be used to determine a feature score threshold for a desirable operating point along the CC. For example, a first threshold may be used when identifying high risk individuals for immediate intervention, and a second threshold may be used when identifying individuals who would benefit from remote health monitoring.

Data, such as data 310, may include information from a broad variety of sources. Some examples of data include information regarding medical history, genetics, activity level, food intake, demographics, geographical information, and involvement in social networks.

Physiological data includes measurements such as blood pressure, glucose level, heart rate, platelet count, blood oxygen content, and temperature, for example.

Medical history information may include, for example, historical information related to immunizations, surgeries, growth, development, medical events (e.g., heart attack,) and medical complications (e.g., hospital readmission, diabetes complication, and asthma attack.) Genetic information may include, for example, history of family diseases, and gene-related markers. Activity level information may include, for example, present motion information, percentage of non-movement to movement, number of steps per day, and frequency of participation in sport activities. Food intake information may include, for example, information related to intake such as frequency, volume or mass, calories, amount of fluid, frequency and amount of alcohol, and percentage of vegetables.

Demographic information may include, for example, gender, race, age, disabilities, mobility, home ownership, employment status, and education history. Geographical information may include, for example, living location, work location, commute information, regularly visited locations, and number of miles driven per week. Social networking information may include, for example, type and frequency of in-person gatherings, percent of in-person social interaction versus electronic social interaction, number of online social networking site memberships, frequency of accessing electronic social networking sites, and number of texts per day.

Other examples of data include a clinician's input such as a logical inference about a disease, or a nurse's recommendation for a change of medication dosage.

The present disclosure describes, among other things, the acquisition of data from different sources, and techniques for selecting relevant and non-redundant data.

A context-aware prediction system may gather data from patients by asking questions, and may also gather data from patients automatically. Data may be gathered locally, for example in a clinician's office, or remotely. Data may be gathered using wired or wireless devices.

In some implementations, physiological or other data may be acquired using a remote monitoring system. For example, remote sensors may capture patient temperature, which may be used as physiological data input to one prediction model, and may be used to create temperature trend or average data as contextual data input for another prediction model.

Figure 4:
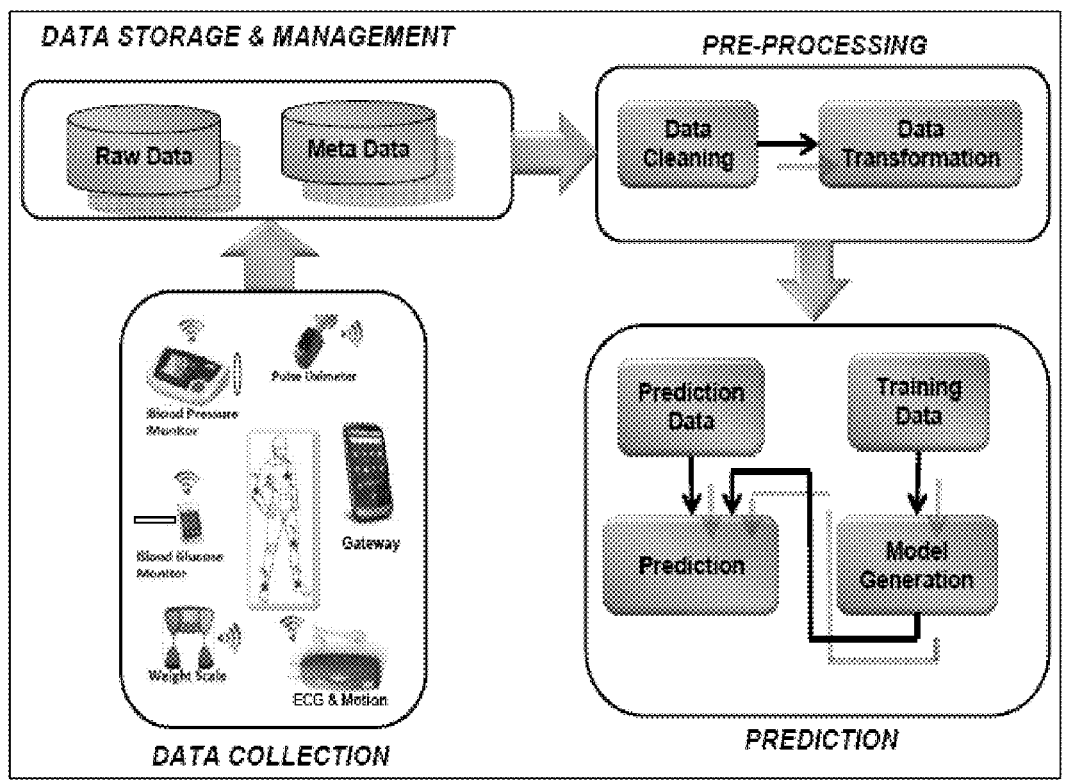
FIG. 4 illustrates an example of a system for remote health monitoring.

FIG. 4 illustrates one embodiment of a context-aware prediction system that uses wireless devices to automatically gather data from a person.

Data collection in the embodiment of FIG. 4 is illustrated using representations for blood pressure monitoring, pulse oximetry, blood glucose monitoring, weight measurement, electrocardiography (ECG), and motion detection, by way of example. Not all of the example data collection devices need to be used for data collection, and further, other data collection devices may additionally or alternatively be used.

A gateway device receives data from collection devices such as the wireless devices illustrated in FIG. 4, or other devices not shown. In one embodiment, a smartphone is used as the gateway. A gateway may also display data that is gathered. A gateway may have an input device which can record manually entered data. In one embodiment, the gateway is a personal computer.

A gateway may connect to a data source using a wireless or wired connection, and may request data, receive the data, and terminate the connection. A gateway may connect to a data source through a public or private communications network.

The gateway device provides the data for storage and management. Storage may be on the gateway. Additionally or alternatively, the gateway may provide the data in whole or in part to another device for storage. Meta data may be associated with the collected data, and in some circumstances, the data collected is itself meta data. Meta data refers to data that provides information about one or more aspects of collected data, such as: time and date of creation, type of data, user who has created the data (e.g. a patient who has taken a blood pressure measurement or a clinician who has entered data regarding patient medications), for example.

A gateway used for acquiring raw data may be different from a gateway that is used for acquiring meta data.

Data collection may be performed across multiple persons to build prediction models for medical conditions or events. During the model-building stage, data collection is performed, and the collected data is stored. The data may be cleaned and transformed as necessary in pre-processing. Pre-processing may be performed as data is being collected, or may be performed on collected data.

Once data has been gathered, the data may be used to generate one or more models relating data to medical conditions or events. The models are used to predict medical conditions or events for an individual or group.

Figure 5:
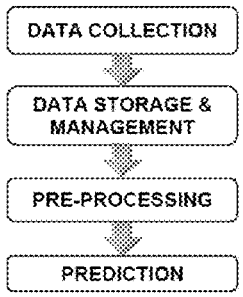
FIG. 5 illustrates an example of event prediction for an individual in a context-aware system.

FIG. 5 illustrates an example of event prediction for an individual in a context-aware system. Data may be collected from the individual, optionally stored and pre-preprocessed, and used with a model to predict medical conditions or events for which the individual may be at higher risk.

Figure 6:
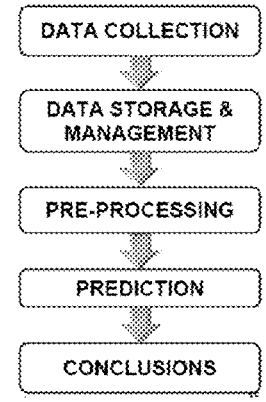
FIG. 6 illustrates an example of how a prediction model may be used to determine conclusions about a group of individuals.

FIG. 6 illustrates an example of how a prediction model may be used to determine conclusions about a group of individuals. Data is collected from multiple subjects, and one or more prediction models determined from the data. From the model(s), conclusions about the group may be formed, and such conclusions may be representative conclusions used to form conclusions regarding larger populations. For example, a model may indicate that individuals in a particular socioeconomic category are more likely to have knee injuries than individuals in other socioeconomic categories. For another example, a model may find patient subgroups of populations that are at high risk of developing diabetes.

Figure 7:
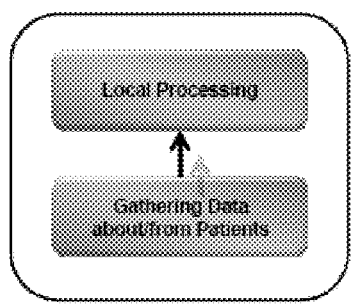
FIG. 7 illustrates local processing of data.

Significant amounts of data may be collected, both for generating prediction models, and for comparing an individual's data to prediction models. As illustrated in FIG. 7, some data processing may be performed on collected data locally, for example on a data-collection device or gateway. Local data processing may include noise reduction, data summation, data normalization, and data fusion.

Figure 8:
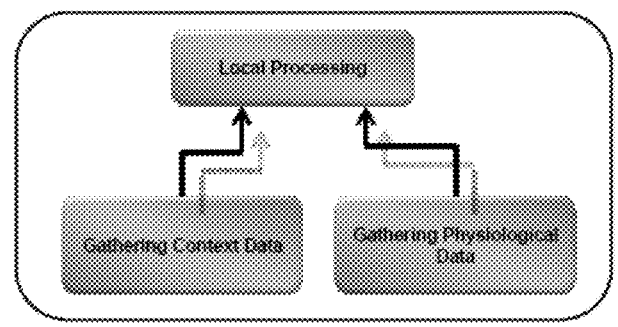
FIG. 8 illustrates local processing on a device that receives data from multiple sources.

FIG. 8 illustrates local processing on a device that receives data from multiple sources.

Figure 9:
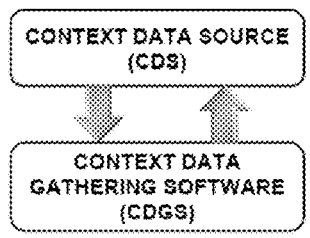
FIG. 9 illustrates data collection by context data gathering software.

FIG. 9 illustrates that data may be collected by context data gathering software (CDGS). For example, a CDGS may retrieve data from an electronic medical record system, an online social network, a web data collector, or other source of data. Data may also be entered manually using a CDGS. A CDGS may reside on a gateway. A CDGS may also reside on a server such as a web-server where data storage occurs.

Figure 10:
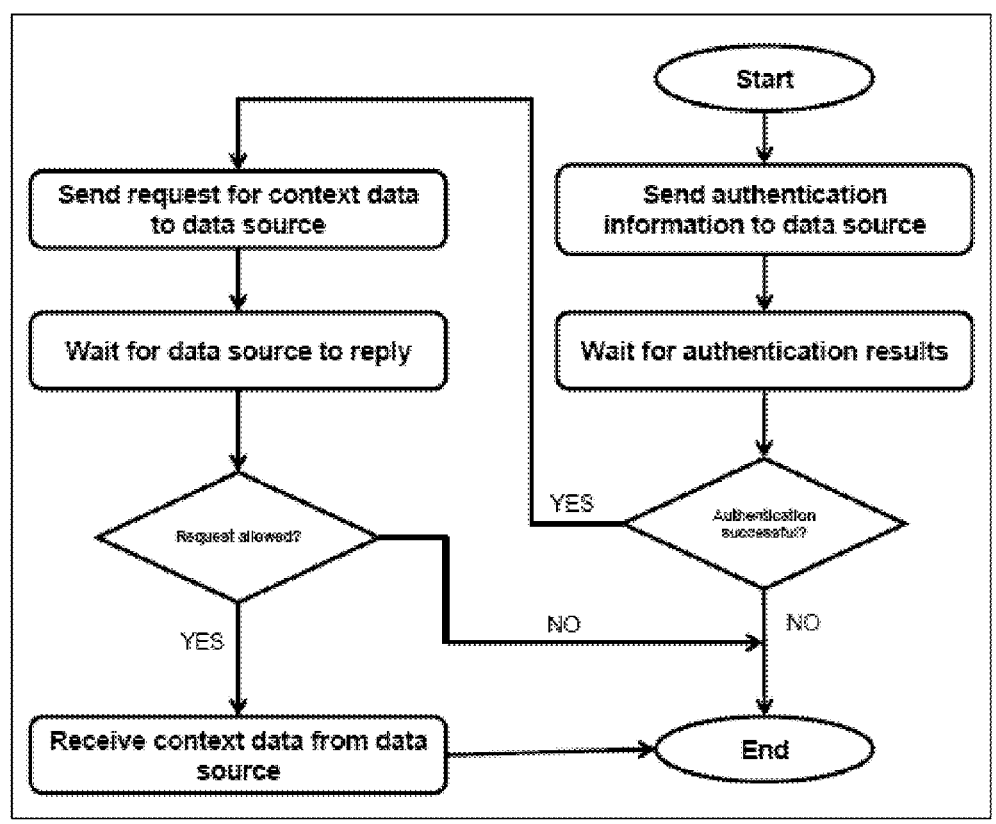
FIG. 10 illustrates data collection by context data gathering software.

FIG. 10 illustrates an example of automatic gathering of data where an electronic data source responds to requests made by a CDGS. As illustrated in FIG. 10, authentication and authorization may be included in the interaction between the CDGS and the electronic data source, for example, for security and privacy reasons.

Figure 11:
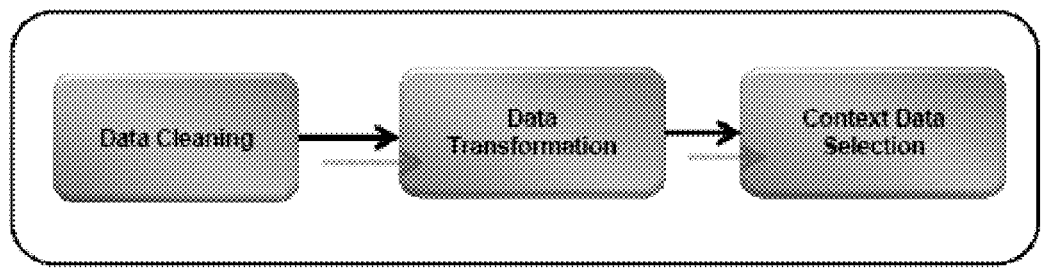
FIG. 11 illustrates an example of pre-processing including data cleaning, data transformation, and context data selection.

As mentioned above with respect to FIG. 4, collected data may be pre-processed before use in generating models or use in determining predictions. FIG. 11 illustrates one embodiment of pre-processing including data cleaning and data transformation, followed by context data selection.

Data cleaning removes noise from collected data and imputes missing values. One example of noise is the time between steps as recorded by an accelerometer pedometer, in which the signal from the accelerometer between steps contains little useful data for a particular prediction.

Data transformation refers to extracting statistical and/or morphological features from gathered data. Data transformation may also contain a dimensionality reduction function. In one example, dimensionality reduction includes selection of a subset of data items gathered in the data collection phase. In another example, dimensionality reduction includes selection of a subset of features extracted by a feature selection process.

Pre-processing may further include selection of context data relevant to the prediction process.

Figure 12:
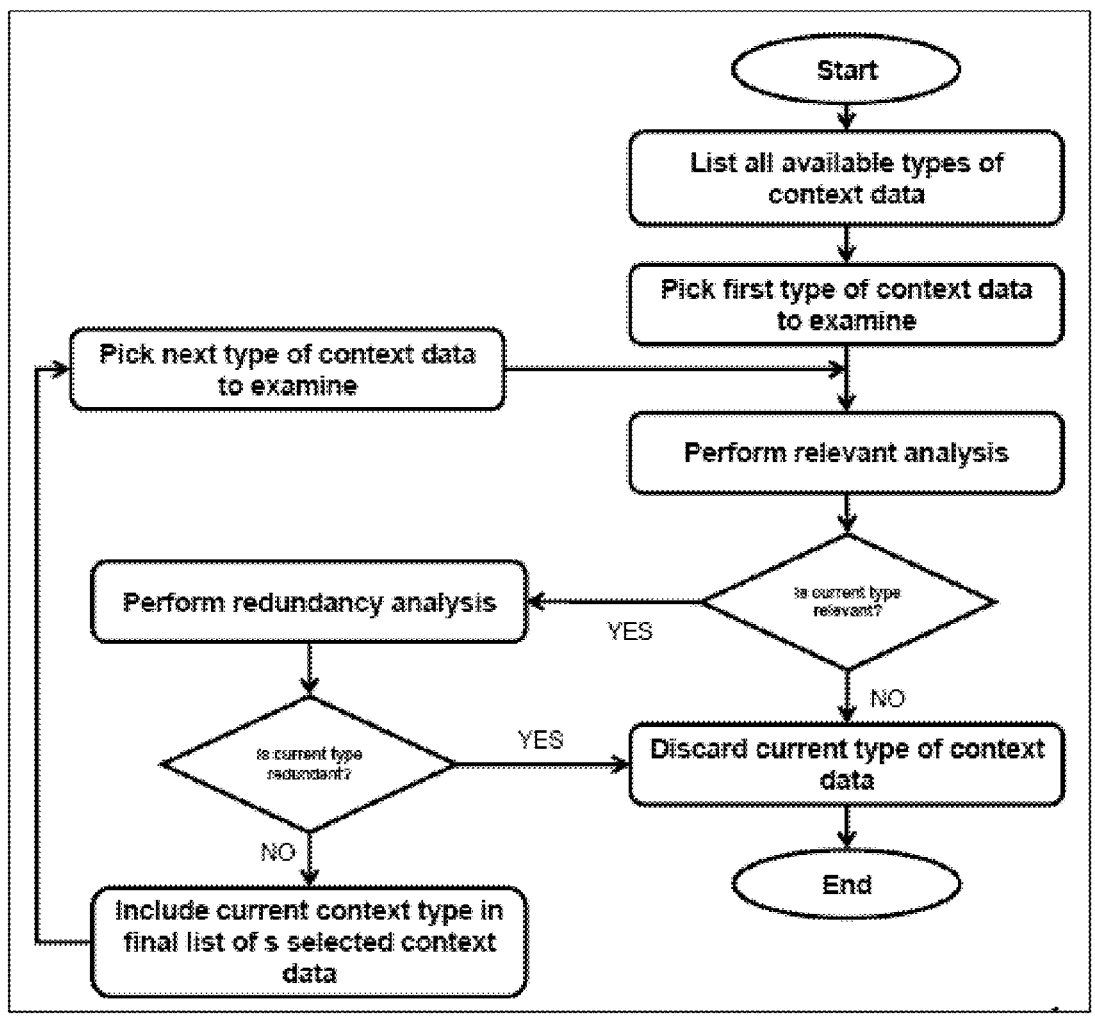
FIG. 12 illustrates an example process for selecting types of data for prediction.

FIG. 12 illustrates one example process for selecting types of data for prediction. As illustrated in the example of FIG. 12, two types of analyses are done: a relevance analysis and a redundancy analysis. Relevance analysis examines whether or not a given type of data is relevant to the prediction task. Redundancy analysis determines if a given type of data is highly correlated with an already selected data type. For example, if income level and model of vehicle driven were highly correlated, these two types of data are redundant to each other.

In one example, Information Gain may be used as a means for calculation of relevance and redundancy measures. A correlation coefficient may be used for data selection analysis.

In one implementation, relevance and redundancy analyses are based on the concept of symmetric uncertainty. The symmetric uncertainty between two discrete random variables X and Y is given by U(X, Y) as follows:

$$U(X, Y) = \frac{2I(X, Y)}{H(X) + H(Y)} \quad (1)$$

where H(X) and H(Y) represent the entropy of random variables X and Y, respectively, and I(X, Y) denotes the information gain between the two variables. I(X, Y) is defined as $$I(X,Y) = H(X) - H(X|Y) \quad (2)$$

The symmetric uncertainty is the normalized information gain and is between 0 and 1, where U=1 indicates that knowing the value of either variable can completely predict the other variable, and U=0 indicates that the two variables are completely independent. The symmetric uncertainty is a measure of correlation between two random variables. An advantage of this measure against other measures, such as correlation coefficient, is that the symmetric uncertainty can capture non-linear correlation between variables.

In one implementation, a prediction technique aims to classify samples of two classes, positive (P) and negative (N). A datum D is irrelevant to the prediction task if $$\min\{U(D,P), U(D,N)\} < thr1 \quad (3)$$

where thr1 is a predefined or user-selected threshold.

In another implementation, there are a set of n features $F=\{f_1, f_2, \ldots, f_n\}$ and a set of outcomes $A=\{a_1, a_2, \ldots, a_h\}$, where a feature $f_i$ is irrelevant to the classification task if $$\min_j(U(f_i, a_j)) < \lambda_R \quad (4)$$

where $\lambda_R$, the relevance threshold, is a design parameter. Relevance analysis eliminate features that are irrelevant to prediction of the outcome.

The remaining m features (m<n) are subject to redundancy analysis to find strongly correlated features. Two features $f_i$ and $f_k$ are considered to be strongly correlated if $U(f_i; f_k) > \lambda_D$; where $\lambda_D$, the redundancy threshold, is a design parameter. The output of the redundancy analysis is a set of feature pairs in the form of $(f_i, f_k)$, which are strongly correlated and either of them can be eliminated according to the correlation analysis. However, these features can be further analyzed for cost-sensitive feature selection by taking into account one or more cost factors associated with gathering, processing, or storage of the data. In one example, the cost-sensitive analysis is done using a graph model.

Figure 13:
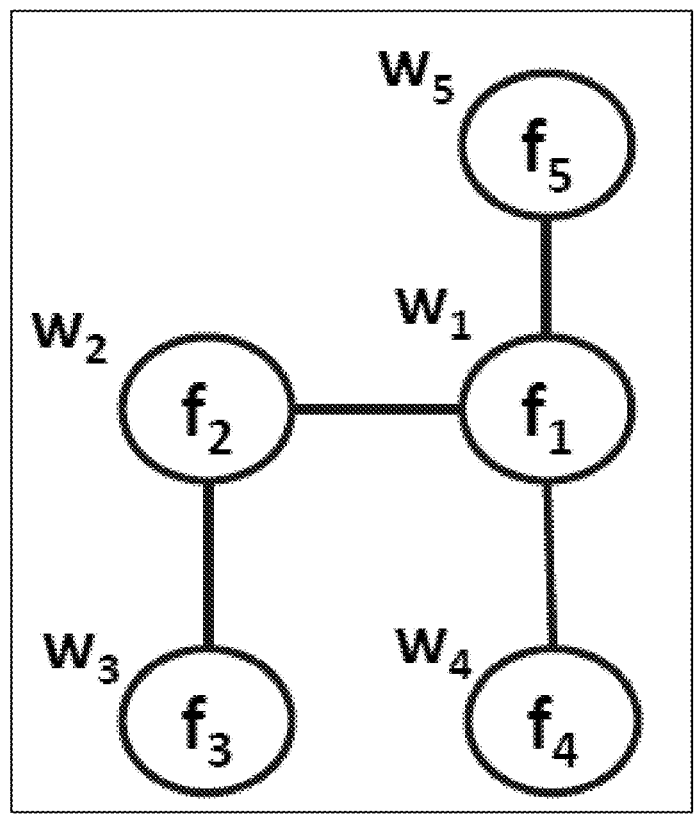
FIG. 13 illustrates an example of a redundancy graph.

Given m relevant features introduced by the relevance analysis and a set of feature pairs $(f_i, f_k)$ generated according to the redundancy analysis, a undirected graph G=(V,E,W) is called a redundancy graph, where V is a set of m vertices $V=\{u_1, u_2, \ldots, u_m\}$ associated with the m relevant features, $E=\{e_1, e_2, \ldots, e_r\}$ is a set of r feature pairs that are strongly correlated, and $W=\{w_1, w_2, \ldots, w_m\}$ is the set of weights, assigned to the vertices, denoting a cost associated with each feature. By way of example, assume that ten features construct the exhaustive set of features, represented by $F=\{f_1, f_2, \ldots, f_{10}\}$. Furthermore, assume that the relevance analysis eliminates five features and hence, the redundancy graph will contain five features. FIG. 13 is illustrative. The cost attributed to each feature is represented by the weight of each vertex. For example, $w_1$ is the cost of $f_1$.

A feature set is next selected using minimum cost feature selection (MCFS). Let all the weights be equal to one unit, that is $W=\{w_1, w_2, w_3, w_4, w_5\}=\{1, 1, 1, 1, 1\}$. In this case, MCFS treats all features equally and thus, the optimal feature set consists of two vertices, specifically $f_1$ and $f_3$. However, if the weight set is modified to $W=\{10, 1, 1, 1, 1\}$, MCFS gives more consideration to vertices with lower weights and accordingly, features $f_4$ and $f_5$ will be favored over $f_1$, and reduced feature set will contain three vertices, for example $f_4$, $f_5$, and $f_3$. As such, the overall cost will be decreased from 11 units to 3 units.

In general terms, cost reduction represents a problem to be solved. Given a redundancy graph G=(V,E,W), the minimum cost feature selection problem is to find a subset of vertices that are not dominated by any other vertex in the graph and a total cost is minimized. The problem is formulated as follows. Assume that $a_{ij}$ is a given binary that encodes existence of edges in the redundancy graph:

$$a_{ij} = \begin{cases} 1, & \text{if}(u_i, u_j) \in V \\ 0, & \text{otherwise} \end{cases} \quad (5)$$

and $x_i$ is a binary variable which determines whether or not a vertex $u_i$ is chosen as a member of the final vertex set:

$$x_i = \begin{cases} 1, & \text{if vertex } u_i \text{ is chosen} \\ 0, & \text{otherwise} \end{cases} \quad (6)$$

The corresponding integer linear programming (ILP) formulation for the MCFS problem is as follows:

$$\text{Minimize} \sum_{i=1}^{m} w_i x_i, \quad (7)$$

subject to:

$$\sum_{j=1}^{m} x_j a_{ij} \geq 1 \ \forall \ i \in \{1, 2, \ldots, m\} \quad (8)$$

$$x_i \in \{0, 1\} \quad (9)$$

The objective function in (7) is to minimize the total cost of the selected vertices (i.e. those with $x_i=1$). The constraint (8) guarantees that each selected vertex is adjacent to at least one more vertex and the constraint in (9) ensures that the variable $x_i$ takes only binary values.

The MCFS problem is similar to the Minimum Cost Dominating Set (MCDS) problem. The MCDS problem is proved to be NP-hard by reduction from the Weighted Set Cover (WSC) problem. The MCFS problem is also NP-hard, as shown by reduction from the WSC problem. Let (S,U,W) be an instance of the WSC problem with the universe U and the family of subsets $S=\{S_1, S_2, \ldots, S_n\}$ each associated with a weight value $w_i$ from the set $W=\{w_1, w_2, \ldots, w_n\}$. Construct a graph G=(V,E,W) as follows: for each set $S_i \in S$, draw a vertex $u_i$ (associated with feature $f_i$) and draw and edge $(u_i, u_j)$ for every pair of $(u_i, u_j) \in S_i$. This forms the vertex set $V=\{u_1, u_2, \ldots, u_n\}$ as well as the edge set E. Furthermore, assign to each vertex $u_i$ (associated with the set $S_i$) the weight value $w_i$ as given by the set W. Now if $C=\{S_i: i \in D\}$ is a feasible solution of the weighted set cover problem, then D is also a solution to the MCFS problem.

A greedy technique for solving the MCFS problem is as follows.

---

Require: Redundancy graph G=(V,E,W)
Ensure: Final vertex set Ω
  Ω = ∅
  for all $u_i \in V$ do
    $V_i$ = {all vertices $u_j$ adjacent to $u_i$}
  end for
  while V ≠ ∅ do
    $V_i \leftarrow \text{argmax}_{V_i} \frac{|V_i|}{w_i}$
    Ω ← Ω ∪ {$u_i$}
    $V_i \leftarrow V_i \setminus \{u_i, u_j\}$ and $V \leftarrow V \setminus \{u_i, u_j\}$
  end while

---

For each vertex $u_i$ in the redundancy graph, the technique first finds all adjacent vertices ($V_i$). It then finds the best candidate vertex to include in the final vertex set Ω. The best candidate is the one with maximum profit. A maximum profit vertex is the one with maximum value of "cardinality of $V_i$ divided by vertex cost $w_i$". The intuition behind selecting such a vertex is that it has a large number of adjacent vertices and a small cost. The technique adds the candidate vertex ($u_i$) to Ω and eliminates $u_i$ and all its neighbors from $V_i$ as well as V. The technique iterates until there are no more vertices in V, indicating that each vertex is either chosen as a final vertex or is dominated by a final vertex.

The greedy technique has a time complexity of O(m log m) where m=|V|. In fact, the main loop in the greedy technique above is the 'while' loop which iterates for O(m) time. The main operation inside the loop is to the vertex with maximum profit (maximum value of "cardinality of $V_i$ divided by vertex cost $w_i$"). This can be done in O(log m) time using a priority heap. Therefore, the greedy technique achieves a time complexity of O(m log m).

The greedy technique achieves a ln n approximation to the MCFS problem. For every vertex $u_i$ selected as maximum profit vertex, define $\theta_i$ as $|V_i|/w_i$ at the time that $u_i$ was picked. Essentially, when $u_i$ is picked, it will dominate a number of adjacent vertices. For each vertex $u_j \in V$, let $u_i$ be the first picked vertex that is adjacent to $u_j$ and dominates it. Let define the cost associated with each dominated vertex $u_j$ be cost($u_j$)=1/$\theta_i$.

Notice that $\Sigma_{j=1}^{m}$cost($u_j$) represents the total cost obtained by the greedy technique. Next, order the vertices in the order that they were dominated. At the time that the kth vertex (call it $u_k$) was dominated, V contained at least m−k+1 vertices. For example, at the very beginning of the technique when the first vertex $u_1$ in $V_i$ is being dominated by the first picked vertex $u_i$, the total number of non-dominated vertices in V is m. When the second vertex $u_2$ is about to be dominated by some neighboring vertex, the number of non-dominated vertices in V is m−1. At that point, the "per-vertex" cost OPT is at most OPT/(m−k+1). For at least one of the $u_i$ (call it U) in OPT, it is thus known that $$\frac{|U \cap V|}{w_i} \geq \frac{m-k+1}{OPT} \quad (10)$$

For the vertex $u_i$ picked by the technique as the most profit vertex, $$\theta_i \geq \frac{(m-k+1)}{OPT}. \quad (11)$$

Therefore, $$\text{cost}(u_k) \leq \frac{OPT}{m-k+1} \quad (12)$$

Over the execution of the greedy technique, the value of k changes from m to 1, and so the total cost of each vertex that the technique removes is at most $$\sum_{k=1}^{m} \frac{OPT}{m-k+1} \leq OPT \ln m. \quad (13)$$

As shown, the greedy technique is a ln m approximation to the MCFS, where m denotes the number of vertices in the redundancy graph.

Real-time feature selection may pose a challenge in some systems. As an example, a wearable sensor node system may be used for remote health monitoring, and may have constraints on processing power, memory, and available energy due to its portability (e.g., wireless access, battery operation). The greedy technique presented above finds a cost-minimized feature set based on the cost of the features. Additionally, the greedy technique itself may be cost-minimized.

Similar to the weighted set cover problem, the MCFS problem belongs to a group of hard problems which are neither able to be approximated in polynomial time nor are fixed parameter tractable. While one can use the ILP approach to find an optimal solution offline (i.e. finding an optimal feature set prior to deploying a wearable sensor node system), the ILP may not be feasible for real-time execution in a constrained system. Thus, for real-time and dynamic feature selection, an approximation is preferred, as long as sufficient accuracy is obtained. The greedy technique presented above has a logarithmic approximation factor (ln m) and yields a time complexity of O(m log m). Ideally, one would like to devise a technique which has an accuracy as close as possible to the ILP solution and a time complexity as close as possible to the greedy approach. For better accuracy, time complexity may be sacrificed.

Without loss of generality, let (ln r) be the approximation ratio of a the feature selection technique that runs ILP on partitioned feature subsets. Also, assume that such a technique runs in $t=c^{m/r}$ time units. The objective is to find an optimal number of partitions that minimize the approximation ratio subject to a time budget (T) for performing feature selection.

Minimize ln $r$ (14)

Subject to:

$t \leq Tt = c^{m/r}$ (15)

$t = c^{m/r}$ (16)

This optimization problem is equivalent to:

Minimize $r$ (17)

Subject to:

$$r \geq \frac{\ln t}{\ln T}$$ (18)

Thus, the optimal number of partitions is $$\dot{r} = \frac{\ln t}{\ln T} = \ln(t-T)$$ (19)

Figure 14:
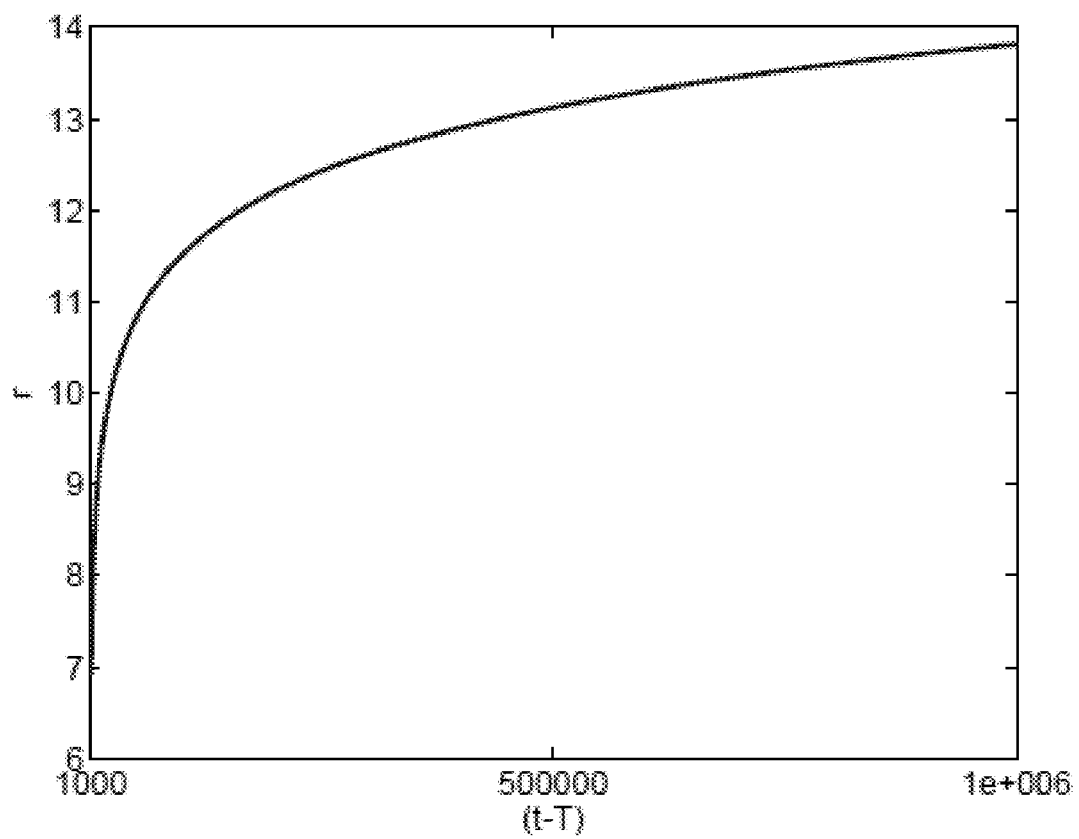
FIG. 14 illustrates an example of partitions versus time budget.

FIG. 14 shows how the number of partitions grows as t-T increases as a result of reduction in the time budget (T). The figure illustrates r for the case when t-T ranges from $10^3$ to $10^6$.

Thus has been described a context-aware prediction system used in a medical environment. It will be clear from the specification that the context-aware prediction system may also be used in other prediction environments, such as for predicting environmental situations, crowd behavior, geological formations, weather patterns, market fluctuations, and other areas in which contextual and outcome data is available for the creation of a model.

Figure 15:
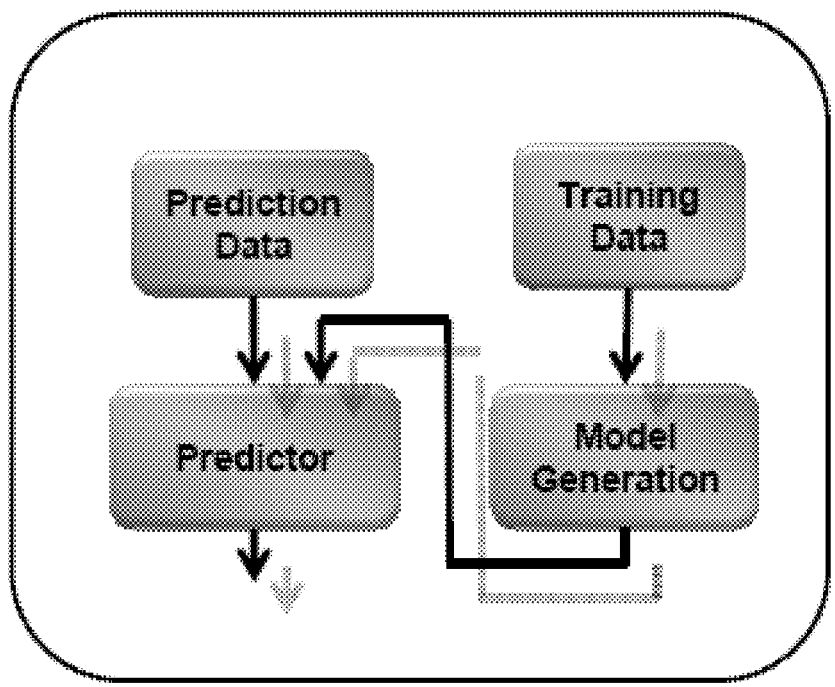
FIG. 15 illustrates an example of model generation and the subsequent use of the model in prediction.

FIG. 15 illustrates an example of model generation and the subsequent use of the model in prediction. Model generation may be implemented, for example, as a regression model that operates on the collected data and provides a mathematical equation that may be used to calculate the probability of a medical condition. 'Training data' in FIG. 15 refers to the data that is being used for generating a model for prediction of a specific medical condition.

'Prediction data' refers to data used along with the prediction model to predict incidence of a specific medical condition. For example, prediction data includes any previously collected data associated with a specific individual for whom a prediction is to be made.

Model generation may alternatively or additionally include one or more of machine learning, pattern recognition, artificial intelligence and statistical inference processes such as classification, regression, and clustering techniques.

With respect to community-based conclusions, in one example, the collected data from a group of patients is used for clustering (also called unsupervised classification) to stratify patients based on contextual factors. This way, similar patients (according to their data) are grouped together (identified by the clustering technique). Thus, a conclusion can be made about patient subgroups. Examples of clustering techniques include K-means clustering, hierarchical clustering, and Gaussian Mixture Model.

Analysis of a Clinical Study—Predictors of Users of a Remote Health Monitoring System One embodiment of the technique for context-aware prediction was used to determine a model for predicting successful outcomes for using a remote health monitoring (RHM) system prior to enrolling a patient in the system.

The use of RHM systems has grown exponentially and has improved patient-provider communication, shared decision making, activation, and self-management in patients with Chronic Heart Failure (CHF). Despite these promising prospects, actual exposure to the use of wireless technologies—defined as accessing the intervention (first use), engaging in the intervention for a substantial period of time (prolonged use), and revisiting the intervention (sustained use)—remain fairly low in patients with CHF. Furthermore, it is unclear what subgroups of patients may benefit from RHM technologies and what user characteristics and contextual factors determine effective use of these systems.

In the CHF study, an RHM system was used to collect daily weight, blood pressure (systolic & diastolic), heart rate, and symptom questions from 16 patients with congestive heart failure. Baseline data including 200 features was also collected from each patient. Examples of such features include demographics, comorbidity, weight, psychosocial attributes (depression, anxiety, quality of life questions), gender, age in years at baseline, marital status, cohabitation, availability of a friend in which to confide, ethnicity, years of education completed, education level, employment status, how well the household lives on its income financially, smoking history, drinking history, average exercise level, height in inches, weight in pounds, and medical insurance.

An analysis of a CHF study was conducted to: 1) examine the predictors of accessing (i.e., first-use of) RHM; and 2) distinguish between users and non-users of RHM by employing advanced data analytics in a group of patients with CHF. The goal was to assess patient adherence by determining whether subgroups of patients with CHF would be more inclined to effectively using RHM systems, and identifying contextual and physiological factors that contribute to such adherence prediction.

The CHF study was a single-arm experimental study with a pre- (baseline) and post- (3 months) test; data from the baseline measures was then used for the predictor analyses. A total of 16 patients (mean age 65.8±6.1, range 58-83) provided consent for the CHF study; however, only 7 patients accessed the developed RHM system and transmitted data (e.g. weight, blood pressure, heart rate, symptom distress) to a centralized information system within 7±2 days of hospital discharge for CHF exacerbation, per study protocol. The baseline data (about 200 attributes) was used for attribute selection and patient classification. All attributes with a missing value were eliminated from data analysis to avoid the effect of missing data imputation on adherence assessment. The remaining 88 attributes were fed into an attribute selection technique followed by a decision table classifier. The classifier was used to distinguish between the two groups of patients (adherent versus non-adherent).

The data was used to build a prediction model based on decision tree classification. Decision tree builds classification models in the form of a tree structure, breaking down the dataset into smaller subsets recursively while at the same time an associated decision tree is incrementally developed. The final result is a tree with decision nodes and leaf nodes. A decision node (a baseline attribute in the dataset) may contain two or more branches. For example, a node that represent patient's age may have three branches for age<50, 50<=age<75, and age>=75. A leaf node (adherence and non-adherence) represents a classification or decision. The topmost node in the tree which is associated with the best predictor is called root. An advantage of developing a prediction technique based on a decision tree classification model is that the decision tree would automatically exclude non-prominent features from considerations for prediction purposes and would explicitly provide a list of prominent features. This is in particular important where the number of baseline features is large. As the results show, however, a very small number of features is sufficient to predict adherence. Essentially these features are those that are used to construct the decision tree. Another advantage of decision tree based classification is that decision trees represent rules, which can be understood by humans and used for decision making.

The decision tree was based on an ID3 technique. A top-down greedy search is performed through the space of possible branches that a feature can make without backtracking to the higher levels of the tree. Constructing branches at each node is based on the measure of entropy and information gain. The decision tree construction process starts from a root node and partitions the data into smaller subsets that contain data items with the similar data types. In order to calculate similarity of a sample (i.e. data instance), entropy is used. Entropy is a measure of homogeneity of the set of samples (e.g. baseline data values). If the sample is completely homogeneous with respect to certain feature, the entropy is zero for that feature (e.g. if all patients have the same age, the entropy with respect to the feature 'age' is zero) and if the sample is an equally divided it has entropy of one (e.g. if all patients have different age values, then entropy of the feature 'age' is one). Given a set S of adherence and non-adherence observations/examples, the entropy of set S relative to this binary classification is $$E(S) = -p(Ad)\log p(Ad) - p(NAd)\log p(NAd)$$

where Ad denotes adherence and NAd refers to non-adherence, and function 'p' is the probability function.

As mentioned, selection of an attribute to test at each node when constructing a decision tree requires that a selection of the most useful attribute for classifying adherence versus non-adherence cases. Information gain is used to find such a node. Information gain measures how well a given attribute separates the training examples according to their target classification. This measure is used to select among the candidate features at each step while expanding a partially constructed tree. Information gain measures the expected reduction in entropy.

$$\text{Gain}(S, f) = \text{Entropy}(S) - \sum_{v \in Values(f)} \frac{|Sv|}{S} \text{Entropy}(Sv)$$

where Values(f) is the set of all possible values for baseline feature f, and Sv the subset of S for which attribute f has value 'v'. The first term in this equation is the entropy of the original collection S and the second term is the expected value of the entropy after S is partitioned using attribute f. The information gain is in fact the expected reduction in entropy caused by partitioning the examples according to the attribute f.

In the CHF study, baseline socio-demographic and clinical characteristics of users and non-users were comparable. However, the attribute selection technique revealed that non-users were less likely to have CHF specialty based care, were more likely to have an automatic internal cardioverter defibrillator, and were more likely to have a history of alcohol use, the three prominent attributes identified by our attribute selection technique. The decision table classifier had both precision and recall of 87.5%, and an F-score of 76.2% for predicting access to RHM.

The analysis of the CHF study showed that a small set of baseline attributes is sufficient to predict access and adherence of patients with CHF to RHM technologies. Furthermore, subgroups of patients with CHF may be more inclined to using RHM interventions. The findings shed light on potential end-users more likely to benefit from RHM interventions.

Analysis of a Clinical Study—Predictors of Successful Health-Improvement Programs One embodiment of the technique for context-aware prediction was used to determine a model for predicting successful outcomes of health-improvement programs. The outcomes were related to changes in body mass index (BMI), waist circumference (WC), high density lipoprotein (HDL) and low density lipoprotein (LDL). Successful outcomes were respectively defined as shown in Table 1.

TABLE 1

| Outcome | Success |
|---|---|
| Body mass index (BMI) | BMI Loss >1 pound/inch$^2$ |
| Waist Circumference (WC) | WC Loss ≥1 inch |
| High density lipoprotein (HDL) | HDL increase |
| Low density lipoprotein (LDL) | LDL decrease |

Context-aware prediction was used to evaluate a clinical study, and identify predictors for future successful health improvement programs using an RHM system.

The evaluated clinical study was performed over six months using an RHM system referred to as Wanda-CVD. The participants in the study were ninety African-American women aged 25-45 years with at least two cardiovascular disease (CVD) risk factors. The study was aimed at reducing risk factors as a preventive measure against CVD.

Wanda-CVD is smartphone-based and designed to provide wireless coaching and social support to participants. In the study, forty-five participants in the intervention group received nutrition and lifestyle education via the Wanda-CVD system. A control group received standard care which included limited education and no remote monitoring.

The smartphone transmits participant measured data in real-time using Wi-Fi and 3G/4G technology. Wanda-CVD analyzes the effects and lifestyle changes that result from social support via automated wireless coaching. The intervention group received four educational classes focused on self-management of diet, nutrition, physical activity and stress reduction. Baselines of cholesterol levels, blood pressure, and BMI were taken, and the participants completed demographic and psychosocial questionnaires. The participants also attended educational classes. The participants were taught how to wear and manage the smartphones and blood pressure monitors. The participants were told that the primary purpose of the smartphone was to track physical activity while providing a user interface and a mechanism for automated feedback. The subjects were able to send/receive unlimited text messages, and had unlimited data plans.

While the majority of the participants in the trial had positive outcomes, many did not benefit. The data from the study was used to find predictors of RHM outcome success, to not only better understand which people succeed using an RHM system, but also to identify a set of screening questions prior to enrolling a patient into an RHM system. This could save time and resources, and help to mold the current health monitoring systems to better suit different populations. Additionally, because dropout rates increase with questionnaire length, developing a prediction model could reduce the burden on participants by identifying more effective questions relating to the objectives and success criteria of a study.

In the clinical study, a variety of physiological and psychological information was gathered from the participants.

During the face-to-face baseline visit and the three and six month follow-up visits, physiological and psychological measurements were taken using anthropometric measures, questionnaires and a software program.

Lipid levels (i.e., total cholesterol, HDL, LDL, and triglycerides) were analyzed using a Cholestech, a small lightweight analyzer designed for point of care testing. BMI was calculated from height and weight measured using a professional grade stadiometer (secca 225 Hite-Mobile) and a high capacity electronic body weight scale (S6600, Summit). Waist circumference was measured by following the standardized procedures recommended in the Anthropometric Standardization Reference Manual. Circumferences were measured to the nearest centimeter using a professional grade anthropometric tape measure.

Participants completed several questionnaires. The questionnaires were grouped into categories, such as those listed in Table 2.

TABLE 2

| Acronym | Description | Purpose |
|---|---|---|
| FAMHX | Demographics-Health History | Family and medical history |
| BRIEFS | Brief Symptom Inventory | Measure of anxiety |
| PHQ | Patient Health Questionnaire | Measure of depressive symptoms |

TABLE 2-continued

| Acronym | Description | Purpose |
|---|---|---|
| MOSSAS | Medical Outcomes Study-SAS | Measure of expected adherence |
| SF | MOS-SF-12 | Measure of quality of life |
| PMT | Protection Motivation Theory | Measure of perceived threat of heart disease |
| STRESS | INTERHEART STRESS | Measure of stress |
| SOCSUP | Perceived Social Support Scale | Measure of available social support |
| INSURA | Insurance Questionnaire | Measure of insurance coverage |

The physiological and psychological measurements provide context data and outcome data for determining predictors of success from an analysis of the clinical study. A goal in analyzing the clinical study was to determine a subset of questions that aim at determining participant CVD study outcome success. Results of the clinical study are provided, followed by a discussion of determining the predictors from an analysis of the clinical study.

The results of the six month study included the following outcomes: 49% of the participants had a reduction in WC, 30% had a decrease of BMI, 60% had an increase in HDL levels, and 55% had a decrease in LDL levels.

In the analysis of the clinical study, several feature selection techniques were evaluated, and a preferred feature selection technique selected based on its ability to identify predictors. Feature selection techniques generally focus on specific metrics to quantify the relevance and/or redundancy of features to find the smallest subset of features providing a maximum amount of useful information for prediction. A goal of feature selection techniques is to eliminate redundant or irrelevant features in a given feature set. Applying an effective feature selection technique not only decreases the computational complexity of the system by reducing dimensionality and redundancy, but also increases performance of the classifier by deleting irrelevant and confusing information.

Two categories of feature selection techniques are filter techniques and wrapper techniques. Filter techniques use a specific metric to score each individual feature (or a subset of features together), and may be faster and much less computationally intensive than wrapper techniques. Wrapper techniques use a classifier to evaluate feature subsets in an iterative manner according to their predictive power.

For the analysis of the clinical study, the wrapper category was selected, and testing was performed on multiple combinations of feature subsets and classifiers. The classifiers used included kNN, BayesNet, SVM, Random Forest, and C4.5DT. For each combination of feature subsets and classifiers, probabilities were assigned to features by the classifiers, and the accuracy of the assignment of probabilities was used to grade the combination. The grades were then used to select a combination of a preferred feature subset and a preferred classifier. Note that the selection of a classifier, as described with respect to analyzing the clinical study, is optional according to the concepts of this disclosure. One classifier may first be selected, and then subsequently used to identify a preferred feature subset.

A characteristic curve (CC) was used to characterize the accuracy of the probability assignments. To create the CC, a sequence of probability thresholds was set, and at each probability threshold, a true positive rate (TPR) and false positive rate (FPR) were determined for features with probabilities above the threshold. The TPR/FPR determination was performed for probability thresholds between a high probability (such that there were no or substantially no encompassed features, and therefore no true positives or false positives) and a low probability (such that all or substantially all features were encompassed, and therefore many false positives along with the true positives). A plot of FPR versus TPR at the different threshold settings results in a CC. The area under the curve (AUC) can then be used to measure the discrimination, or the ability to correctly classify participant outcome for each outcome category of the clinical study. The AUC was then available to compare various combinations of features subsets and classifiers.

The Random Forest classifier with one hundred trees was selected as the classifier for the clinical study, as it provided quick and generally accurate prediction results.

Figure 16:
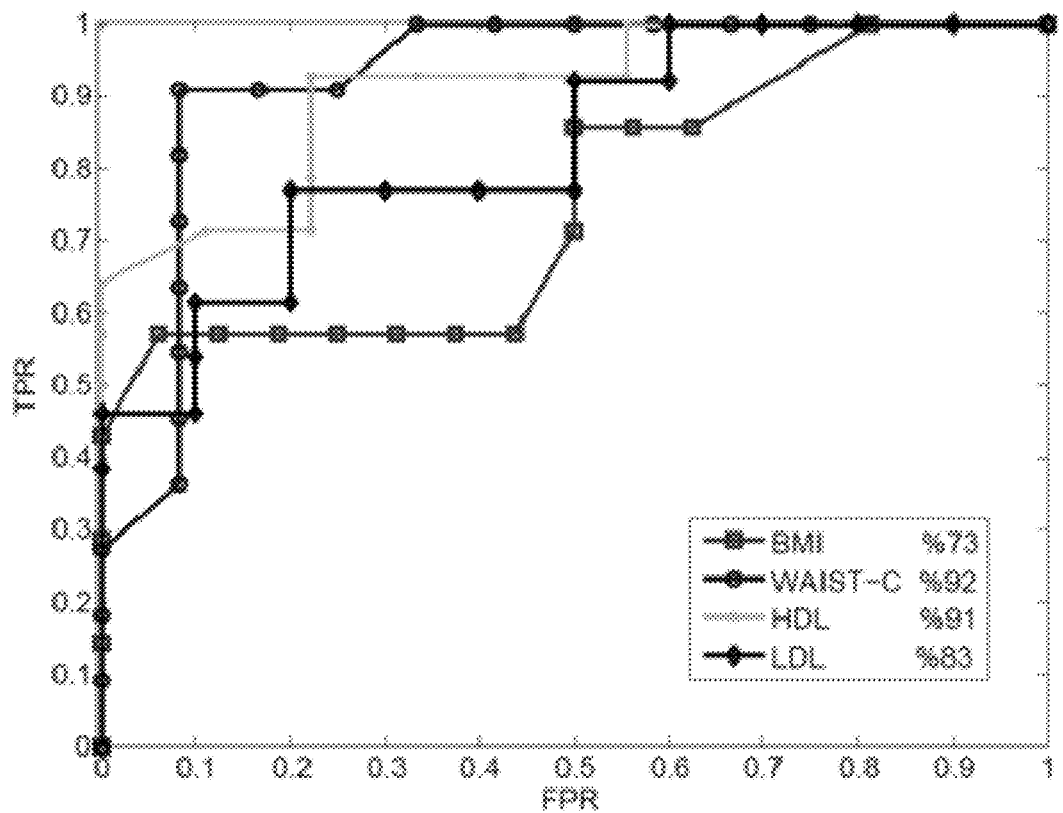
FIG. 16 illustrates characteristic curves for an outcome.

FIG. 16 illustrates a CC for each of the WAIST-C, BMI, HDL, and LDL outcomes for the data from the clinical study. The AUC for WAIST-C is 92.4%, while the AUC for BMI is 73%. The lower AUC for BMI than for WC bolsters prior research that WC is more closely linked to cardiovascular disease risk factors than is BMI, illustrating that the AUC technique provides information useful in comparing predictors to each other for a given outcome, in addition to the other advantages described in this disclosure.

The features selected as predictors for outcomes based on the clinical study data are next described.

Waist Circumference (WC).

Approximately 48% of the participants had lost at least one inch of WC at the end of the six month intervention, which was previously defined as a successful outcome. The features identified as predictors for WC outcome success were mostly associated with the categories PMT, INSURA, SF, and FAMHX. The following features were selected using the Pearson correlation coefficient:

1) PMT14: (Thoughts about your health) I only know how to cook with salt and fat?
    Available responses ranged from "Strongly Agree" to "Strongly Disagree."
2) INSURA: (General Information) Are you currently covered by any of the following health insurances? Government insurance (Medicare, Medicaid, Veteran's Administration health plan, military medical plan, or other government-reimbursed care).
    Available response is binary, either "Yes" or "No."
3) SF-3A: During the past 4 weeks, how much of the time have you had this problem with your work or other regular daily activities as a result of your physical health? Accomplished less than you would like.
    Available responses ranged from "All of the time" to "None of the time."
4) FAMHX: Grandparents having Stroke/TIA or a Mother with Heart Disease.
    Available response is binary, either "Yes" or "No."

The participants that were closer to 'disagree' for a question regarding only knowing how to cook with salt and fat did well in the study, while those that were agreeable were unsuccessful at a reduction in waist circumference (i.e., had a non-successful WC outcome). Those that had government insurance and were of low income did decrease WC (i.e., had a successful WC outcome). Of the participants who had functional problems at work or while performing daily activities, 40% had a successful WC outcome. Participants with first degree relatives having a stroke or heart disease also had a successful WC outcome.

Body Mass Index (BMI).

Approximately 30% of the participants had lost 1 pound per $inch^2$ (or more) at the end of the six month intervention, previously defined as a successful BMI outcome. (57% of those with successful BMI outcomes also had successful WC outcomes). The features identified as predictors for BMI outcome success were mostly associated with the categories: STRESS and SOCSUP. The following features were selected using the Pearson correlation coefficient:

1) STRESS4: Have you experienced a major life event in the past year such as marital separation, divorce, loss of job, retirement, business failure, violence, death or major injury or illness of a close family member, death of a spouse or other major stress?
    Available response is binary, either "Yes" or "No."
2) STRESS1: Do you experience stress at home?
    Available responses ranged from "Never experienced stress at home," to "Have permanent stress at home."
3) SOCSUP7: I can count on my friends when things go wrong.
    Available responses ranged from "Strongly Agree" to "Strongly Disagree."

Of the participants that experienced a major life event in the past year (STRESS4), 89% did not have a successful BMI outcome. The participants that responded that they had experienced permanent or several periods of stress at home also did not have a successful BMI outcome, and 86% that did have a successful BMI outcome experienced less stress at home. With the exception of one, all participants that had a successful BMI outcome had a friend that they could count on (SOCSUP7).

Lipid Profile HDL.

Approximately 58% of the participants succeeded in increasing their HDL levels, previously defined as a successful HDL outcome. The features identified as predictors for HDL outcome success were mostly associated with the categories: PMT, MOSSAS, SF, and PHQ. The following features were selected:

1) PMT29: My family won't eat healthy foods even if I cook them.
    Available responses ranged from "Strongly Agree" to "Strongly Disagree."
2) PMT23: If I want to, I can eat foods with less salt and fat.
    Available responses ranged from "Strongly Agree" to "Strongly Disagree."
3) MOSSAS9: Limit sodium in diet (ate less than 2500 mg per day).
    Available responses ranged from "All the time" to "None of the time."
4) SF3B: During the past 4 weeks, how much of the time have you had this problem with your work or other regular daily activities as a result of your physical health? Were limited in the kind of work or other activities.
    Available responses ranged from "All of the time" to "None of the time."
5) PHQ9: Thoughts that you would be better off dead or of hurting yourself in some way.
    Available responses ranged from "Not at all" to "Nearly every day."

It can be seen that PMT is also an important feature in predicting HDL levels. Another important predictor was adherence to diet—participants that limited their sodium in their diet had successful HDL outcomes. Participants who had functional problems at work or while performing daily activities, had unsuccessful HDL outcomes. Participants that had thoughts of being dead or hurting themselves (PHQ9) had unsuccessful HDL outcomes.

Lipid Profile LDL.

Approximately 57% of the participants reduced their LDL levels, previously defined as a successful LDL outcome. The features identified as predictors for LDL outcome success were mostly associated with the categories: BRIEFS, PHQ, and PMT. The following features were selected:
1) BRIEFS2: How much were you distressed by being: Suddenly scared for no reason.
   Available responses ranged from "Not at all" to "Extremely."
2) BRIEFS5: How much were you distressed by spells or terror or panic.
   Available responses ranged from "Not at all" to "Extremely."
3) PHQ4: Over the last 2 weeks, how often have you been bothered by: Feeling tired or having little energy.
   Available responses ranged from "Not at all" to "Nearly every day."
4) PHQ7: Over the last 2 weeks, how often have you been bothered by having: Trouble concentrating on things, such as reading the newspaper or watching television.
   Available responses ranged from "Not at all" to "Nearly every day."
5) PMT20: My chances of having a heart disease are very small.
   Available responses ranged from "Strongly Agree" to "Strongly Disagree."
6) PMT25: Compared to other people my age, my chances of getting heart disease in the future are not very high.
   Available responses ranged from "Strongly Agree" to "Strongly Disagree."

Participants with high anxiety as a result of distress from sudden fear (BRIEFS2) had unsuccessful LDL outcomes. Of the participants that were distressed by spells or terror or panic (BRIEFS5), 83% had unsuccessful HDL outcomes. 75% of the participants that had responded closer to "Often" regarding feeling tired or having little energy (PHQ4) had unsuccessful HDL outcomes. Also, all the participants that had trouble concentrating on things such as reading the newspaper or watching television had unsuccessful HDL outcomes.

The analysis of the clinical study provided a set of preferred features for predicting successful outcomes, for each of the outcomes WC, BMI, HDL, and LDL. Going forward, an individual or a group of individuals exhibiting one or more of the features in a set of features may be identified as being at risk for the associated WC, BMI, HDL, or LDL outcome. The individual features in a set may be weighted to correspond the relative predictive ability of the features in the set, or may be normalized. Weighting and/or normalization may provide increased resolution in the prediction process, to provide the appropriate level of intervention, care or support, for example.

An embodiment of the disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as application-specific integrated circuits ("ASICs"), programmable logic devices ("PLDs"), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

What is claimed is:

1. A method of context-aware prediction of medical conditions, comprising:
   by a first computing device executing instructions from a non-transitory computer-readable medium for:
      receiving contextual data related to at least one of environmental, physiological, behavioral, and historical context;
      receiving outcome data related to at least one outcome;
      creating a feature set from the contextual data;
      selecting a subset of features from the feature set;
      assigning a score to each feature in the subset of features according to a probability that the feature is a predictor of the at least one outcome;
      generating a characteristic curve for the at least one outcome from the subset of features, the characteristic curve based on the scores of the features in the subset of features;
      calculating an area under the characteristic curve;

identifying, using the area under the characteristic curve, whether the subset of features is a suitable predictor for the at least one outcome;

responsive to identifying that the subset of features is a suitable predictor for the at least one outcome, generating a prediction model relating the subset of features to the at least one outcome; and providing to a display device for display a prediction of a likelihood of occurrence of the at least one outcome by applying the prediction model to data received from a monitoring device, wherein generating the characteristic curve includes iteratively:

setting a probability threshold;

selecting a feature group from the subset of features, wherein, for each feature in the feature group, the assigned score is greater than the probability threshold;

determining for the contextual data of features in the feature group a true positive rate and a false positive rate of prediction of the outcome; and plotting the true positive rate and the false positive rate for the probability threshold.

2. The method of claim 1, wherein the characteristic curve is one of a plurality of characteristic curves, further comprising comparing the area under the characteristic curve to areas under other characteristic curves in the plurality of characteristic curves and identifying a preferred predictor based on the comparing.

3. The method of claim 1, wherein the characteristic curve is one of a plurality of characteristic curves, further comprising comparing the area under the characteristic curve to areas under other characteristic curves in the plurality of characteristic curves and identifying a preferred scoring technique based on the comparing.

4. The method of claim 1, further comprising:
receiving additional contextual data; and
predicting an outcome based on the additional contextual data using the prediction model.

5. The method of claim 4, wherein the additional contextual data includes data regarding a group of individuals, and the predicted outcome is a prediction of the outcome for the group of individuals.

6. The method of claim 1, wherein the contextual data includes data from a plurality of sources.

7. The method of claim 1, wherein the contextual data includes data relating to a plurality of individuals.

8. The method of claim 1, wherein the contextual data includes data taken at a plurality of times.

9. The method of claim 1, wherein the contextual data comprises a weight, a blood pressure, a heart rate, and a symptom response, and wherein the outcome data comprises a use of a monitoring device; further comprising determining whether a subject is using the monitoring device by applying the prediction model to the contextual data.

10. The method of claim 1, wherein the contextual data comprises a body mass index, a waist circumference, a high density lipoprotein, a low density lipoprotein, and a questionnaire associated with a subject; and wherein the outcome data comprises an effectiveness of a health-improvement program, a body mass index loss, a waist circumference loss, a high density lipoprotein increase, or a low density lipoprotein decrease of the subject.

11. The method of claim 1, wherein the outcome data comprises a medical condition of a subject, the medical condition including a chronic health failure or diabetes.

12. The method of claim 1, wherein receiving the contextual data further comprises receiving the contextual data at a predefined interval.

13. A system for context-aware prediction of medical conditions, comprising:

a first computing device comprising a memory including processor-executable instructions and a processor configured to execute instructions from the memory;

wherein the instructions include instructions for the processor to:

receive contextual data and outcome data;

create a feature set from the contextual data;

select a plurality of feature subsets from the feature set;

apply each of the plurality of feature subsets and the outcome data to a classifier, and determine a score for each of the plurality of feature subsets;

select a preferred feature subset based on the score for each of the plurality of feature subsets; and generate a prediction model of an outcome using the preferred feature subset; and an interface providing access to the prediction model by a second computing device;

wherein the prediction model is configured to input subject data received from a monitoring device, make a prediction based on the received subject data regarding a likelihood of the outcome occurring, and output the prediction to the second computing device, wherein the outcome data represents at least one outcome, and wherein the instructions to determine the score for each of the plurality of feature subsets includes instructions for the processor to, for each feature subset:

use the classifier to determine a probability measure for each feature in the feature subset, the probability measure being an indication of how predictive the feature is for an outcome of the at least one outcome;

create a characteristic curve of true positive rate versus false positive rate, wherein each point of the characteristic curve represents a portion of the feature set, and each portion of the feature set is selected based on a probability measure threshold; and calculate the score as an area under the characteristic curve.

14. The system of claim 13, wherein the instructions further include instructions for the processor to cluster the contextual data, and create the feature set from at least a portion of the clustered contextual data.

15. The system of claim 14, wherein the clustered contextual data includes multiple data clusters, and wherein the instructions to create the feature set include instructions to create a plurality of features sets from respective ones of the multiple data clusters.

16. The system of claim 13, wherein the outcome data includes data representing a plurality of different outcomes.

17. The system of claim 13, wherein the instructions further include instructions for the processor to receive additional contextual data, and predict an outcome from the additional contextual data using the prediction model.

* * * * *